United States Patent [19]

Bore et al.

[11] 4,270,919

[45] Jun. 2, 1981

[54] PROCESS FOR ASSESSING THE PRESENCE OF OXIDIZING AGENTS ON OF KERATIN FIBERS

[75] Inventors: Pierre Bore, Montfermeil; Arnaud De Labbey, Aulnay-Sous-Bois, both of France

[73] Assignee: L'Oreal, Paris, France

[21] Appl. No.: 55,229

[22] Filed: Jul. 6, 1979

[30] Foreign Application Priority Data

Jul. 12, 1978 [FR] France ................................ 78 20847

[51] Int. Cl.$^3$ ..................... G01N 31/22; G01N 33/40; G01N 33/52
[52] U.S. Cl. ............................... 23/230 B; 23/230 R; 422/56
[58] Field of Search ......................... 23/230 B, 230 R; 422/56

[56] References Cited

FOREIGN PATENT DOCUMENTS 2623261  1/1977  Fed. Rep. of Germany ............. 422/56

OTHER PUBLICATIONS

English Translation of Czechoslovak Pat. No. 125,017 (published 1/15/68)–Translation by U.S. P.T.O. on 10/5/73.

*Primary Examiner*—Barry Richman
*Attorney, Agent, or Firm*—N. Jerome Rudy

[57] ABSTRACT

A process for assessing the state of surface oxidation of keratin fiber(s), especially human hair, which results following treatment with, inter alia, peroxides and bromates. This process involves applying a porous support to the wet fiber(s) to be assessed, which support has previously been impregnated with an oxidation indicator which is a solution of iodide ions, the normality of which is from 0.2 N to 10 N, the solution also containing from 20 g/liter to 200 g/liter of solubilized starch in a buffered acid medium, and, while the porous support is in contact with the fiber(s), applying to the support a solution of a strong acid, as developer, and subsequently removing the support and examining whether or not there has been a change in the initial coloration of the support.

10 Claims, No Drawings

PROCESS FOR ASSESSING THE PRESENCE OF OXIDIZING AGENTS ON OF KERATIN FIBERS

DESCRIPTION

This relates to a process for assessing the state of surface oxidation of keratin fibres.

It is known that, during a cosmetic treatment of human hair, such as a permanent-waving, bleaching or colouring treatment, it can be desirable for the expert to check whether the applications and rinses have been carried out satisfactorily by evaluating certain characteristics of the hair. Amongst these characteristics, the state of oxidation of the hair may be mentioned in particular because numerous hair-treatment products require the application, either simultaneously or subsequently, of an oxidising agent such as hydrogen peroxide or other peroxide or a per-salt. Numerous experiments which we have carried out have shown how difficult it is to remove traces of oxidising agents from the hair following an oxidizing treatment. This is significant since the result of a subsequent treatment frequently epends on the initial state of oxidation of the hair.

It is also known that the iodide/iodine reduction oxidation system, in an acid medium, gives rise to a brown coloration when it is brought into contact with an oxidizing agent. The commercially available papers using this system are not suitable for assessing the state of oxidation of the hair; in fact, they most frequently exhibit the disadvantage of being selective, that is to say of being sensitive to certain oxidizing agents but insufficiently sensitive to others. Thus, commercially available indicator paper of this type generally has a good sensitivity to hydrogen peroxide such that aounts of as little as a few parts per million can be detected, but, on the other hand, will be insufficiently sensitive to bromates. Bromates are however commonly used oxidizing agents in cosmetics. Other systems based on the enzymatic destruction of certain peroxides are also known, but such systems are still too selective and therefore not sufficiently universal and thus do not apply to all the oxidizing agents used in cosmetics.

The object of the present invention is therefore to provide a simple and rapid test which has a high sensitivity with respect to all the oxidizing agents commonly used in cosmetics. Such a test enables the hairdresser to evaluate the state of oxidation of the hair of his customers and, in particular, to check whether the rinses carried out have been adequate or whether they should be continued. According to the present invention, such a test typically involves applying to wet hair, at various points on the head of hair if necessary, a small strip of paper impregnated with an oxidation indicator containing a high concentration of solubilized starch and of iodide ions in a buffered acid medium. The contact time can be very short, for example about ten seconds. A drop of a strong acid, used as a developer, is then poured onto the small strip; if there is a change from white to deep brown, it can be deduced therefrom that oxidizing agents still remain on the hair and that rinsing should consequently be continued; if there is no change, the absence of a change means that the rinsing has fully achieved its purpose and that the oxidizing agents have been sufficiently removed. We have found that this test makes it possible to detect amounts of oxidizing agent as little as a few parts per million.

The present invention therefore provides a process for assessing the state of surface oxidation of keratin fibers and, in particular, the presence in human hair of an oxidizing agent such as hydrogen peroxide or other peroxide or a per-salt, which process comprises applying a porous support, such as a small strip of paper, to the wet fibers to be assessed, which support has previously been impregnated with an oxidation indicator which is a solution of iodide ions, the normality of which is from about 0.2 N to about 10 N, the solution also containing from about 20 g/liter to about 200 g/liter of solubilized starch in a buffered acid medium, and, while the porous support is in contact with the fibres, applying to the support a solution of a strong acid as developer and subsequently removing the support and examining whether or not there has been a change in the initial coloration of the support.

Thus and as is easily obvious and readily apparent, practice of the present invention actually possibilitates good and reliable indication of the residual presence of oxidizing agent in the keratin fibers, such as and especially human hair, being tested which in effect and by logical deduction reveals and is a valid indicative assessment of the actual state of surface oxidation of the keratin fibers being examined.

The concentration of iodide ions in the indicator solution used to impregnate the porous supports is preferably from 2 N to 6 N and the concentration of solubilized starch in the said solution is preferably from 50 g/liter to 150 g/liter.

In a preferred embodiment, the impregnated porous support is placed in contact with the hair for 1 to 20 seconds; the solution of strong acid used as a developer is typically a one normal solution of hydrochloric acid; about 1 to 2 drops of developer are caused to act on the porous support placed in contact with the wet hair.

The present invention also provides an oxidation indicator intended to be used, in the process defined above, for impregnating porous supports, such as small strips of paper, which are then dried, which comprises a solution of iodide ions, the normality of which is from about 0.2 N to about 10 N, this solution also containing from about 20 g/liter to about 200 g/liter of solubilised starch in a buffered acid medium.

In a preferred embodiment, the solution of oxidation indicator used for impregnating the porous support contains potassium iodide; its pH is about 4.7; the buffer medium is formed by a mixture of acetic acid and sodium acetate; the concentration of potassium iodide in the indicator solution used for impregnating the porous supports is from about 20 g/liter to about 1,250 g/liter.

In order to prevent the oxidation of the iodides during the drying of the small strips impregnated with the oxidation indicator, sodium bisulphite or other reducing agent is conveniently added to the impregnating solution at a concentration of 0.25 g/liter to about 1 g/liter.

The following Examples further illustrate the present invention.

EXAMPLE 1

An oxidation indicator is prepared using 15 g of potassium iodide and 2.5 g of solubilized starch, and also 30 mg of sodium bisulphite, which are dissolved in 25 $cm^3$ of a buffer medium formed by a mixture of acetic acid and sodium acetate; 20 $cm^3$ of water are added thereto. The pH is about 4.7.

A small strip of paper, having a surface area of 0.25 $cm^2$, is impregnated with 3.3 mg of potassium iodide, 1.1 mg of solubilized starch and 0.006 mg of sodium bisulphite, that is to say the oxidation indicator prepared above; the small strip of paper is then dried. In order to carry out the test, the small strip of paper is applied to wet hair for about 10 seconds.

Using a dropping bottle, a drop of a one normal solution of hydrochloric acid, as developer, is applied onto the small strip of paper placed in contact with the wet hair, if desired. A check is then carried out to determine whether or not there has been a change from white to deep brown. The brown coloration which appears is all the more intense, the greater is the proportion of solubilized agent.

The assessment of the state of oxidation of hair using the indicator of Example 1 is given below. In these Examples hair bleached with a mixture of hydrogen peroxide and persulphate, and hair which has been permanently waved, in which case neutralisation of the permanent wave is carried out with a solution of bromates, is used.

EXAMPLE 2

A 1 g swatch of natural hair is bleached with a mixture of hydrogen peroxide of 10 volumes strength and 20% strength sodium persulphate solution in order to achieve a strong bleaching action.

After bleaching, this swatch is rinsed with running water for 30 seconds. The following results are obtained with this test as a function of the number of rinses:

1st rinse: amount of oxidizing agent;
  (in parts per million): >100 ppm
2nd rinse: amount of oxidizing agent: 50 ppm
3rd rinse: amount of oxidizing agent: 30 ppm
4th rinse: amount of oxidizing agent: <10 ppm

EXAMPLE 3

A 1 g swatch of natural hair is permanently wave using a commercially available permanent-waving liquid containing 9% of ammonium thioglycolate. After this reduction step, the swatch is neutralised with an 18% strength solution of sodium bromate. The swatch is subjected to 5 30-second rinses with running water. After application and developing with one normal hydrochloric acid, the test described above gives the following results:

1st rinse: amount of bromates
  (in parts per million); >100 ppm
2nd rinse: amount of bromates: 80 ppm
3rd rinse: amount of bromates: 30 ppm
4th rinse: amount of bromates: 10 ppm The following Example demonstrates that the test is applicable to synthetic or other keratin fiber(s).

EXAMPLE 4

If wool is subjected to the same bleaching process as described in Example 2, it can be shown that, after a first one-minute rinse with running water, the resulting proportion of oxidizing agent is of the order of 50 ppm. It becomes less than 10 ppm after a second one-minute rinse with running water.

The tests of Examples 2 to 4 show that the oxidation indicator according to the invention makes it possible to detect amounts of oxidizing agent which are as small as a few parts per million. In contrast to the known iodide/iodine reduction oxidation systems, the reduction oxidation system of this invention possesses a high sensitivity with respect to the oxidizing agents in common use in cosmetics, in particular with respect to hydrogen peroxide and bromates. In fact, in the case of these oxidizing agents, 10 parts per million are easily detected.

The small strips of paper can be mounted on a rigid plastic support such as a tab. This mounting renders the application easier and can, in particular, prevent the finger of the person carrying out the application from coming into direct contact with the small impregnated strip of paper.

The small strips can be packaged in individual pouches, protected from the light, and this makes it possible to keep them for a long period without the oxidation indicator losing its effectiveness. Thus, the small strips of paper, which are ready for use, can be provided to the expert, namely the hairdresser, with a bottle of developer. It will be appreciated, therefore, that the test of the present invention can be carried out particularly simply and rapidly by persons not skilled in laboratory techniques, because it suffices to place the small strip of paper in contact with the wet hair for about ten seconds and then to pour a drop of developer onto this small strip in order to know whether traces of oxidizing agent remain on the hair.

It should be noted that test(s) performed in accordance with the present invention require the step of developing with strong acid when residual bromates are present in the keratin fibers undergoing examination for the desired assessment.

We claim:

1. Process for determining by test the relative amount of residual oxidizing agent present in keratin fibers which have been subjected to treatment with an oxidizing composition that is at least partially comprised of a bromate material so as, by deductive rationalization therefrom, to be enabled to assess the apparent state of surface oxidation existant in said treated fibers, which process comprises:

(a). applying to a wet sample of the fibers to be tested a pre-impregnated porous support of given and generally substantially light coloration; said support having been previously impregnated with (a'). an oxidation indicator solution comprised of: (i) iodide ions having a normality in said solution of between about 0.2 N and about 10 N and (ii) solubilized starch in effectively buffered acid medium containing a concentration in said solution of between about 20 and about 200 grams per liter of said starch; then (b). with and while said porous support in (a) is maintained in contact with said wet fibers being tested, applying to said support a solution of a strong acid as a developer; and subsequently (c). removing said support and examining same to see if there has been any discernable change whatsoever in and of the initial coloration of the support.

2. Process according to claim 1, in which the concentration of iodide ions in the indicator solution is from 2 N to 6 N and the concentration of solubilized starch in the solution is from 50 g/liter to 150 g/liter.

3. Process according to claim 1, in which the solution of strong acid is a one normal solution of hydrochloric acid.

4. Process according to claim 1, in which the support is contacted with the fibers for from 1 to 20 seconds.

5. Process according to claim 1, in which one or more drops of developer are applied to the support when in contact with the wet fibers.

6. Process according to claim 1, in which the indicator solution contains from 20 to 1250 g/liter of potassium iodide.

7. Process according to claim 1, in which the indicator solution has a pH of about 4.7 and the buffer is a mixture of acetic acid and sodium acetate.

8. Process according to claim 1, in which the indicator solution contains 0.25 to 1 g/liter of sodium bisulphite.

9. The method of claim 16 wherein said bromate-containing oxidizing composition is additionally comprised of an oxidizing reagent selected from the Group consisting of peroxides, per-salts and mixtures thereof.

10. The process of either of claims 1 or 9 wherein the keratin fibers are human hair.

* * * * *